(12) United States Patent
Liphardt

(10) Patent No.: US 8,416,410 B1
(45) Date of Patent: Apr. 9, 2013

(54) CONJUGATE RATIO ADJUSTABLE LENS SYSTEM

(75) Inventor: Martin M. Liphardt, Lincoln, NE (US)

(73) Assignee: J.A. Woollam Co., Inc, Lincoln, NE (US)

( * ) Notice: Subject to any disclaimer, the term of this patent is extended or adjusted under 35 U.S.C. 154(b) by 464 days.

(21) Appl. No.: 12/799,447

(22) Filed: Apr. 26, 2010

(51) Int. Cl.
*G01J 4/00* (2006.01)
(52) U.S. Cl. .................................................... 356/369
(58) Field of Classification Search .................. 356/369
See application file for complete search history.

(56) References Cited

U.S. PATENT DOCUMENTS

| | | | |
|---|---|---|---|
| 4,527,858 A * | 7/1985 | Takahashi et al. | 359/206.1 |
| 4,764,784 A * | 8/1988 | Torikoshi et al. | 396/79 |
| 5,418,136 A | 5/1995 | Miller et al. | 435/5 |
| 5,468,606 A | 11/1995 | Bogart et al. | 435/5 |
| 5,482,830 A | 1/1996 | Bogart et al. | 435/5 |
| 5,494,801 A | 2/1996 | Bogart et al. | 435/7.34 |
| 5,494,829 A | 2/1996 | Sandstrom et al. | 435/518 |
| 5,541,057 A | 7/1996 | Bogart | 435/5 |
| 5,550,063 A | 8/1996 | Bogart | 436/518 |
| 5,552,272 A | 9/1996 | Bogart | 435/6 |
| 5,608,526 A * | 3/1997 | Piwonka-Corle et al. | 356/369 |
| 5,629,214 A | 5/1997 | Crosby | 436/518 |
| 5,631,171 A | 5/1997 | Sandstrom | 436/518 |
| 5,633,757 A * | 5/1997 | Park | 359/650 |
| 5,639,671 A | 6/1997 | Bogart et al. | 436/518 |
| 5,869,272 A | 2/1999 | Bogart et al. | 435/7.32 |
| 5,917,594 A | 6/1999 | Norton | 356/327 |
| 5,955,377 A | 9/1999 | Maul et al. | 436/518 |
| 6,323,946 B1 | 11/2001 | Norton | 356/327 |
| 6,485,703 B1 | 11/2002 | Cote | 424/9.1 |
| 6,583,877 B2 | 6/2003 | Norton | 356/369 |
| 6,587,282 B1 * | 7/2003 | Wang et al. | 359/797 |
| 6,804,004 B1 | 10/2004 | Johs et al. | 356/369 |
| 6,879,449 B2 * | 4/2005 | Wang et al. | 359/785 |
| 6,950,182 B1 | 9/2005 | Liphardt et al. | 356/237.1 |
| 7,057,717 B1 | 6/2006 | Liphardt et al. | 356/237.2 |
| 7,075,649 B1 | 7/2006 | Johs et al. | 356/369 |
| 7,075,650 B1 | 7/2006 | Johs et al. | 356/369 |
| 7,180,084 B2 * | 2/2007 | Weiss et al. | 250/559.4 |
| 7,317,530 B2 | 1/2008 | Liphardt et al. | 356/369 |
| 7,336,361 B1 | 2/2008 | Liphardt et al. | 356/369 |
| 7,345,762 B1 | 3/2008 | Liphardt et al. | 356/369 |
| 7,385,697 B2 | 6/2008 | Woollam et al. | 356/369 |
| 7,385,698 B1 | 6/2008 | Welch et al. | 356/369 |
| 7,468,794 B1 | 12/2008 | Liphardt et al. | 356/369 |
| 7,489,400 B1 | 2/2009 | He et al. | 356/369 |
| 7,518,725 B1 | 4/2009 | Liphardt et al. | 356/369 |
| 7,522,279 B1 | 4/2009 | Liphardt et al. | 356/364 |
| 2002/0024669 A1 * | 2/2002 | Danner et al. | 356/369 |
| 2003/0214730 A1 * | 11/2003 | Wang et al. | 359/797 |
| 2006/0186361 A1 * | 8/2006 | Weiss et al. | 250/559.45 |
| 2009/0027786 A1 * | 1/2009 | Hung et al. | 359/826 |

* cited by examiner

*Primary Examiner* — Roy M Punnoose
(74) *Attorney, Agent, or Firm* — James D. Welch

(57) ABSTRACT

A lens system which allows easy relative adjustment of the position of at least two elements therein to minimize the effects of aberration, having particularly relevant application in ellipsometers, polarimeters, reflectometers and spectrophotometers finite size source is imaged onto a sample.

20 Claims, 4 Drawing Sheets

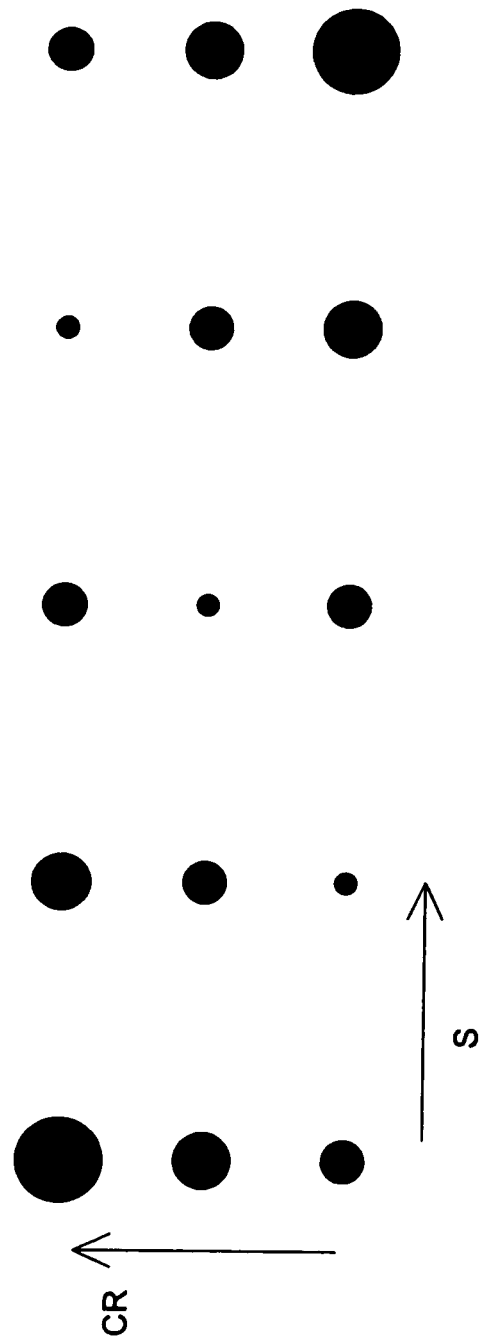

CONJUGATE RATIO ADJUSTABLE LENS SYSTEM

TECHNICAL FIELD

The present invention relates to lens systems, and more particularly to a lens system which allows easy relative adjustment of the position of at least two elements therein to minimize the effects of aberration, having particularly relevant application in ellipsometers, polarimeters, reflectometers and spectrophotometers finite size source is imaged onto a sample.

BACKGROUND

It is known to apply focused beams of electromagnetic radiation to investigate samples using ellipsometers, polarimeters, reflectometers and spectrophotometers. Numerous Patents describe this, such as:

U.S. Pat. No. 7,522,279 to Liphardt et al.;
U.S. Pat. No. 7,518,725 to Liphardt et al.;
U.S. Pat. No. 7,057,717 to Liphardt et al.;
U.S. Pat. No. 7,075,649 to Johs et al.;
U.S. Pat. No. 6,950,182 to Liphardt et al.;
U.S. Pat. No. 7,489,400 to He et al.;
U.S. Pat. No. 7,317,530 to Liphardt et al.;
U.S. Pat. No. 7,468,794 to Liphardt et al.;
U.S. Pat. No. 7,075,650 to Johs et al.;
U.S. Pat. No. 7,385,698 to Welch et al.;
U.S. Pat. No. 7,385,697 to Woollam et al.;
U.S. Pat. No. 7,345,762 to Liphardt et al.;
U.S. Pat. No. 6,804,004 to Johs et al.;
U.S. Pat. No. 7,336,361 to Liphardt et al.;

The forgoing Patents are all incorporated by reference into the specification.

In addition, a computer search for Patents having words "conjugate ratio" and "ellipsometer" or "ellipsometery" provided U.S. Pat. Nos. 6,583,877; 6,485,703; 6,323,946; 5,955,377; 5,917,594; 5,869,272; 5,639,671; 5,631,171; 5,629,214; 5,552,272; 5,550,063; 5,541,057; 5,494,829; 5,494,801; 5,482,830; 5,468,606; 5,418,136.

To avoid confusion and because it is the basis of the present invention, it is specifically noted at this point that, while the present invention system has certain similarities to lens systems which magnify an image at a screen, the present invention is not applied as magnifying, (ie. zoom), lens system. In particular, a magnifying lens system is applied to a scenario in which the screen (eg. a camera screen), and the imaged subject viewed at said screen remain at the same locations as the image at the screen is magnified. The present invention is not concerned with magnification, and instead for a set conjugate ratio, adjusts the configuration of lens elements to image a substantially point source of electromagnetic radiation onto a screen or sample in a manner which minimizes the effects of aberration. Thus, a substantially optimally focused spot size is achieved.

Even in view of the prior art, need remains for new lens configurations which are suitable for application in sample investigating systems, to enable flexibility in providing focused beams at samples where the effects of aberration are minimized. In particular, a lens system which would allow, for any set "conjugate ratio", ie.:

$$\frac{\text{the distance from a source to said lens system}}{\text{the distance from said lens system to said sample}}$$

reducing the effects of aberration of beam focus on the sample, without physically moving a source; sample or detector.

Finally, for general interest, it is noted that the "object distance" is the distance from a source to lens, the "image distance" is the distance from said lens system to a sample such that the equation:

$$\frac{1}{\text{object distance}} + \frac{1}{\text{image distance}} = \frac{1}{\text{focal length}}$$

is satisfied, for paraxial beams.

DISCLOSURE OF THE INVENTION

The present invention is a method of minimizing the effect of aberration caused by a focusing lens system, thereby minimizing a beam spot size at a point whereat it impinges on an image plane. It comprises the steps of:

a) providing a source of electromagnetic radiation having a finite size, and a lens system located at an object distance from said source of electromagnetic radiation, such that an image of said source is formed at an image plane at an image distance from said lens system, said lens system comprising at least two groupings of lens elements, each grouping comprising a selection from the group consisting of:
  a single element; and
  a plurality of lens elements.

Said lens system further comprises means for securing lens elements at intended distances from one another; and allowing for adjustment of distance between two, of said at least two, groupings of lens elements.

Said method continues with:

b) configuring the system to position said source of electromagnetic radiation at an object distance from said lens system to direct a beam thereof through said lens system and impinge at said image plane;

c) adjusting the spacing between at least two, of the at least two, groupings of lens elements so that the effects of aberration, hence, spot size of the beam where it impinges on said image plane become substantially minimized.

Said method can further comprise:

d) configuring the system to position said source of electromagnetic radiation at an object distance from said lens system, which differes from that set in step b, to direct a beam thereof through said lens system and impinge at a resulting image plane;

e) adjusting the spacing between at least two, of the at least two, groupings of lens elements so that the effects of aberration, hence, spot size of the beam where it impinges on a resulting image plane become substantially minimized.

(Note, that the image plane position varies with object distance, as per the equation in the Background Section, but the same approach to adjustment of distance between the spacing between at least two, of the at least two, groupings of lens elements applies for any set object distance, so that the effects of aberration, hence, spot size of the beam where it impinges on a resulting image plane, becomes substantially minimized).

Said method can involve the source and lens system are part of an ellipsometer, polarimeter, reflectometer or spectrophotometer comprising:
- said source of electromagnetic radiation;
- said lens system;
- a sample support located in said image plane; and
- a detector;

wherein a sample to be investigated is positioned on said sample support.

Said method can involve that said system provided further comprises:
- a rotatable or rotating polarizer between said source of electromagnetic radiation and said sample support; and
- an rotatable or rotating analyzer between said sample support and said detector;

with the system being an ellipsometer or polarimeter.

Said method can further involve that said ellipsometer or polarimeter system comprises:
- at least one rotatable or rotating compensator between at least one location selected from the group consisting of:
  - between said polarizer and said sample support; and
  - between said support for said sample support and said detector.

The present invention is further an ellipsometer or polarimeter comprising:
- a source of electromagnetic radiation;
- a polarizer;
- a lens system;
- a sample support with a sample placed thereupon;
- an analyzer; and
- a detector.

Said source of electromagnetic radiation has a finite size, and a lens system located at an object distance from said source of electromagnetic radiation, such that in use an image of said source is formed at an image plane at an image distance from said lens system. Said lens system comprises at least two groupings of lens elements, each grouping comprising a selection from the group consisting of:
- a single element; and
- a plurality of lens elements.

Said lens system further comprises means for securing lens elements at intended distances from one another; and allows for adjustment of distance between two, of said at least two, groupings of lens elements.

Said ellipsometer or polarimeter system can involve that the means for securing lens elements at intended distances from one another comprise a tube in which said lens elements are placed, and in which at least the distance between two, of said at least two groupings of lens elements, is effected by the presence of one or more spacers therebetween.

Said ellipsometer or polarimeter system can involve there being two groups of lens elements separated by a spacer.

Said ellipsometer or polarimeter system can provide that the number of lens elements in each group is independently selected from the group consisting of:
- a single lens element; and
- a plurality of elements.

Said ellipsometer or polarimeter system can provide that there are three groups of lens elements, each said group being separated by a spacer from an adjacent group.

Said ellipsometer or polarimeter system can provide that said one or more spacers are tubular in shape and sized to fit precisely inside said tubular shaped means for securing lens elements at intended distances from one.

The present invention is further a reflectometer or spectrophotometer comprising:
- a source of electromagnetic radiation;
- a lens system;
- a sample support; and
- a detector.

Said source of electromagnetic radiation has a finite size, and a lens system is located at an object distance from said source of electromagnetic radiation, such that in use an image of said source is formed at an image plane at an image distance from said lens system. Said lens system can comprise at least two groupings of lens elements, each grouping comprising a selection from the group consisting of:
- a single element; and
- a plurality of lens elements.

Said lens system further comprises means for securing lens elements at intended distances from one another; and allows for adjustment of distance between two, of said at least two, groupings of lens elements.

Said reflectometer or spectrophotometer system can involve the means for securing lens elements at intended distances from one another comprises a tube in which said lens elements are placed, and in which at least the distance between two, of said at least two groupings of lens elements, is effected by the presence of one or more spacers therebetween.

Said reflectometer or spectrophotometer system can involve that there are two groups of lens elements separated by a spacer.

Said reflectometer or spectrophotometer system can involve the number of lens elements in each group being independently selected from the group consisting of:
- a single lens element; and
- a plurality of elements.

Said reflectometer or spectrophotometer system can involve that there are three groups of lens elements, each said group being separated by a spacer from an adjacent group.

Said reflectometer or spectrophotometer system can involve said one or more spacers are tubular in shape and sized to fit precisely inside said tubular shaped means for securing lens elements at intended distances from one.

The present invention is further a spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:
- before said stage for supporting a material system;
- after said stage for supporting a material system, and
- both before and after said stage for supporting a material system.

In use, when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system.

Said spectroscopic rotating compensator material system investigation system further comprises a lens system comprising at least two groupings of lens elements, each grouping comprising a selection from the group consisting of:
  a single element; and
  a plurality of lens elements.
Said lens system further comprises means for securing lens elements at intended distances from one another; and for allowing for adjustment of distance between two, of said at least two, groupings of lens elements.

Said spectroscopic rotating compensator material system investigation system can involve that the means for securing lens elements at intended distances from one another comprises a tube in which said lens elements are placed, and in which at least the distance between two, of said at least two groupings of lens elements, is effected by the presence of one or more spacers therebetween.

Said spectroscopic rotating compensator material system investigation system can involve that there are two groups of lens elements separated by a spacer.

Said spectroscopic rotating compensator material system investigation system can involve that the number of lens elements in each group is independently selected from the group consisting of:
  a single lens element; and
  a plurality of elements.

Said spectroscopic rotating compensator material system investigation system can involve that there are three groups of lens elements, each said group being separated by a spacer from an adjacent group.

Said spectroscopic rotating compensator material system investigation system can involve that the number of lens elements in each group is independently selected from the group consisting of:
  a single lens element; and
  a plurality of elements.

Said spectroscopic rotating compensator material system investigation system can involve that said one or more spacers are tubular in shape and sized to fit precisely inside said tubular shaped means for securing lens elements at intended distances from one.

It is noted that the object distance can be set by moving a source of a beam of electromagnetic radiation, or by moving a lens system.

The present invention will be better understood by reference to the Detailed Description and associated Drawings.

BRIEF DESCRIPTION OF THE DRAWINGS

FIG. 3 demonstrates the Conjugate Ratio vs. Spacing between lens groups.

DETAILED DESCRIPTION

Figure 1A:
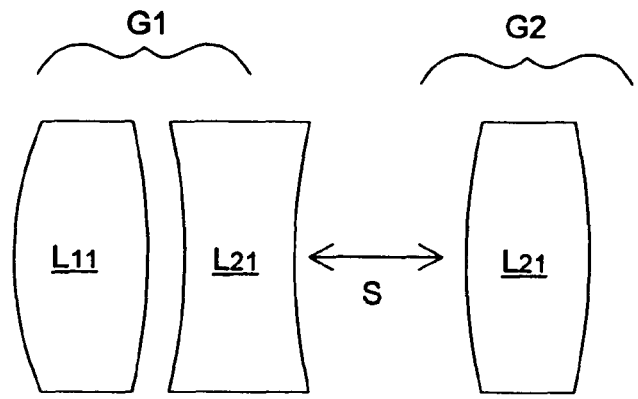
FIGS. 1a-1c demonstrate lens groups.
Figure 1B:
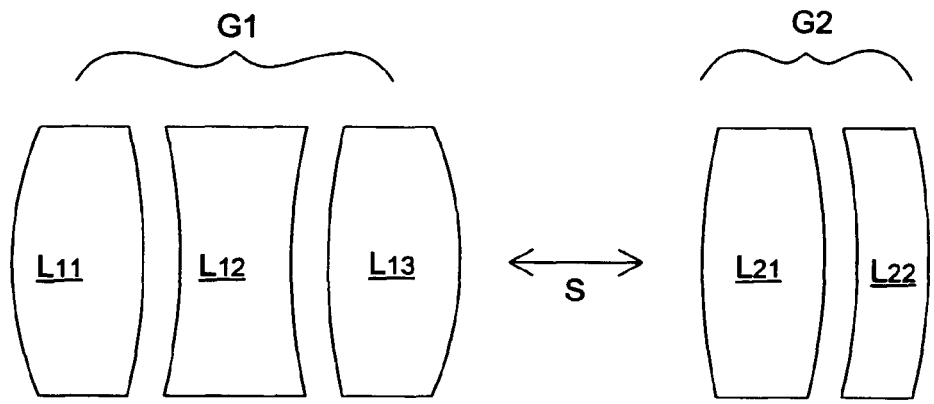
Figure 1C:
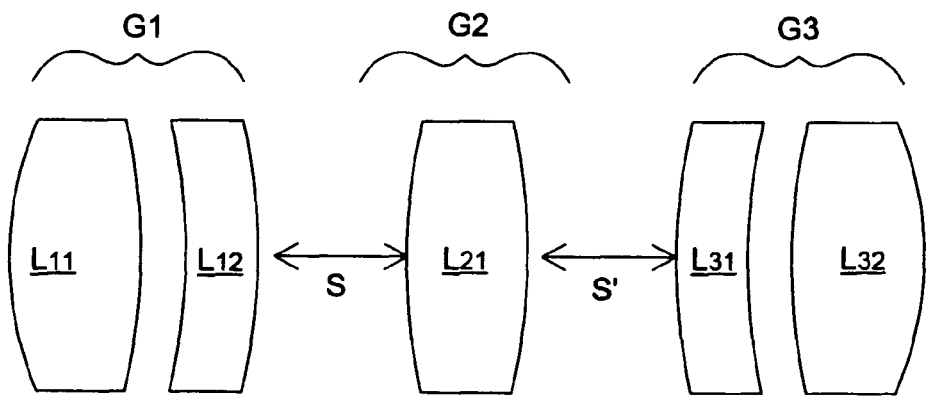

Turning now to FIGS. 1a-1c, demonstrated are lens groups (G1) and (G2). As a non-limiting example FIG. 1a shows a group (G1) contains two lens elements (L11) (L12), and a group (g2) contains a single lens element (L21). Note that the groups (G1) and (G2) are separated by a space (S). FIG. 1b shows another non-limiting example wherein group (G1) contains three elements (L11) (L12) (L13), and groups (G2) contains two lens elements (L21) (L22). FIG. 1c shows another non-limiting example wherein group (G1) contains two lens elements (L11) (L12), and a group (G2) contains one len's element (L21), and a third group (G3) contains two lens elements (L31) (L32).

Figure 2A:
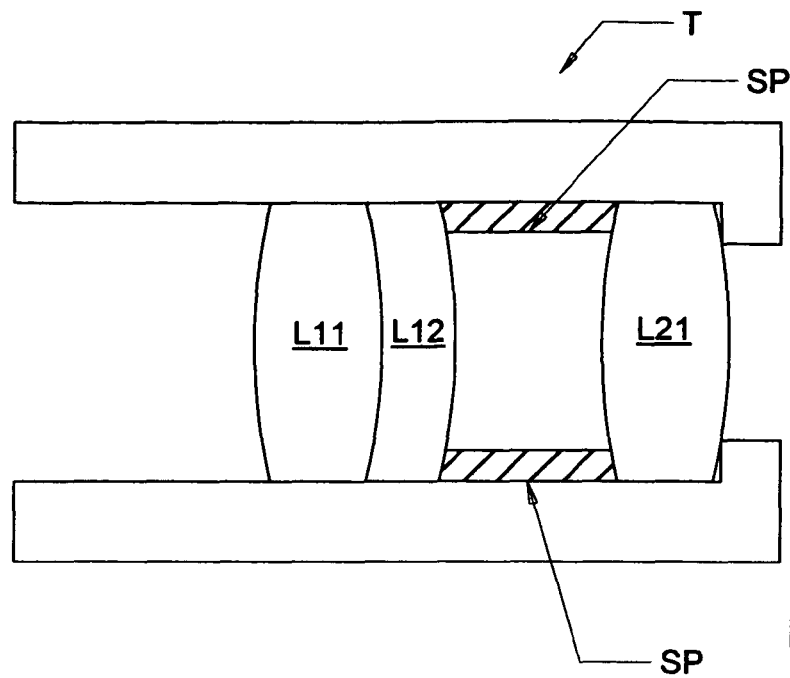
FIGS. 2a-2b demonstrate use of spacers in a tube to separate lens groups.
Figure 2B:
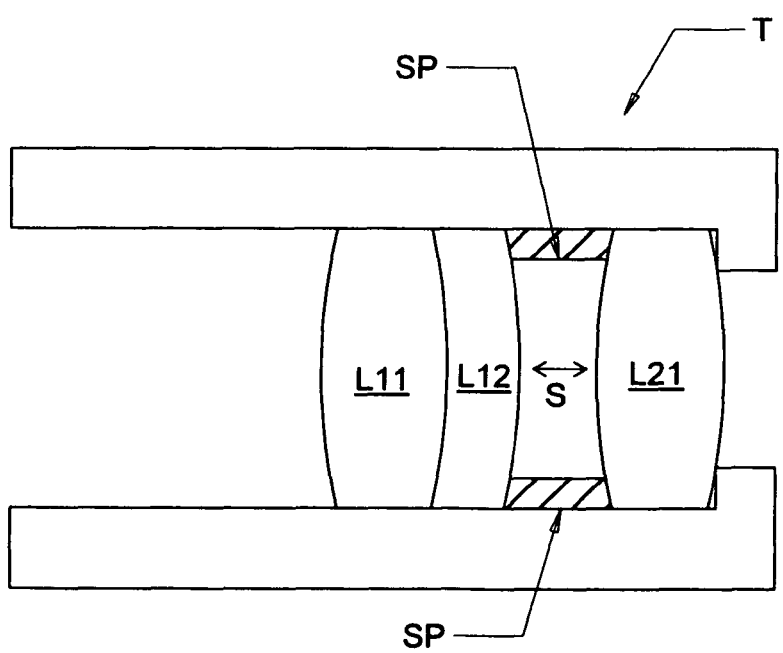

FIGS. 2a-2b demonstrate use of spacers (SP) in a tube (T) to separate two lens groups. FIG. 2a exemplifies the case where on group contain lens elements (L11) (L12), and the other of which contains one element (L21), said groups being separated by a spacer (SP) inside said tube (T). FIG. 2b exemplifies the case of FIG. 16a where the spacer (SP) is shorter. A change in spacer length effectively changes the Conjugate Ratio (CR):

$$\frac{\text{the distance from a source to said lens system}}{\text{the distance from said lens system to said sample}}$$

of the lens system, where the lens system performs optimally;

FIG. 3 demonstrates that how a Conjugate Ratio (CR) vs. Spacing (SP) between lens groups. This demonstrates the benefit provided by the present invention. For a set conjugate ratio, adjustment of the spacing between at least two lens elements, or groups of lens elements, allows a user to minimize the effects of lens aberration, thereby providing imaging a point source of electromagnetic radiation onto a sample at a substantially minimum spot size.

An application of such a lens system is in an ellipsometer, polarimeter, reflectometer, spectrophotometer or the like system, where there is present a source of electromagnetic radiation and a sample supporting stage. A lens system can be fixed at a location therebetween and the Conjugate Ration (CR) set to enable very good focus of a beam from said source, on a sample placed on said stage.

Figure 4:
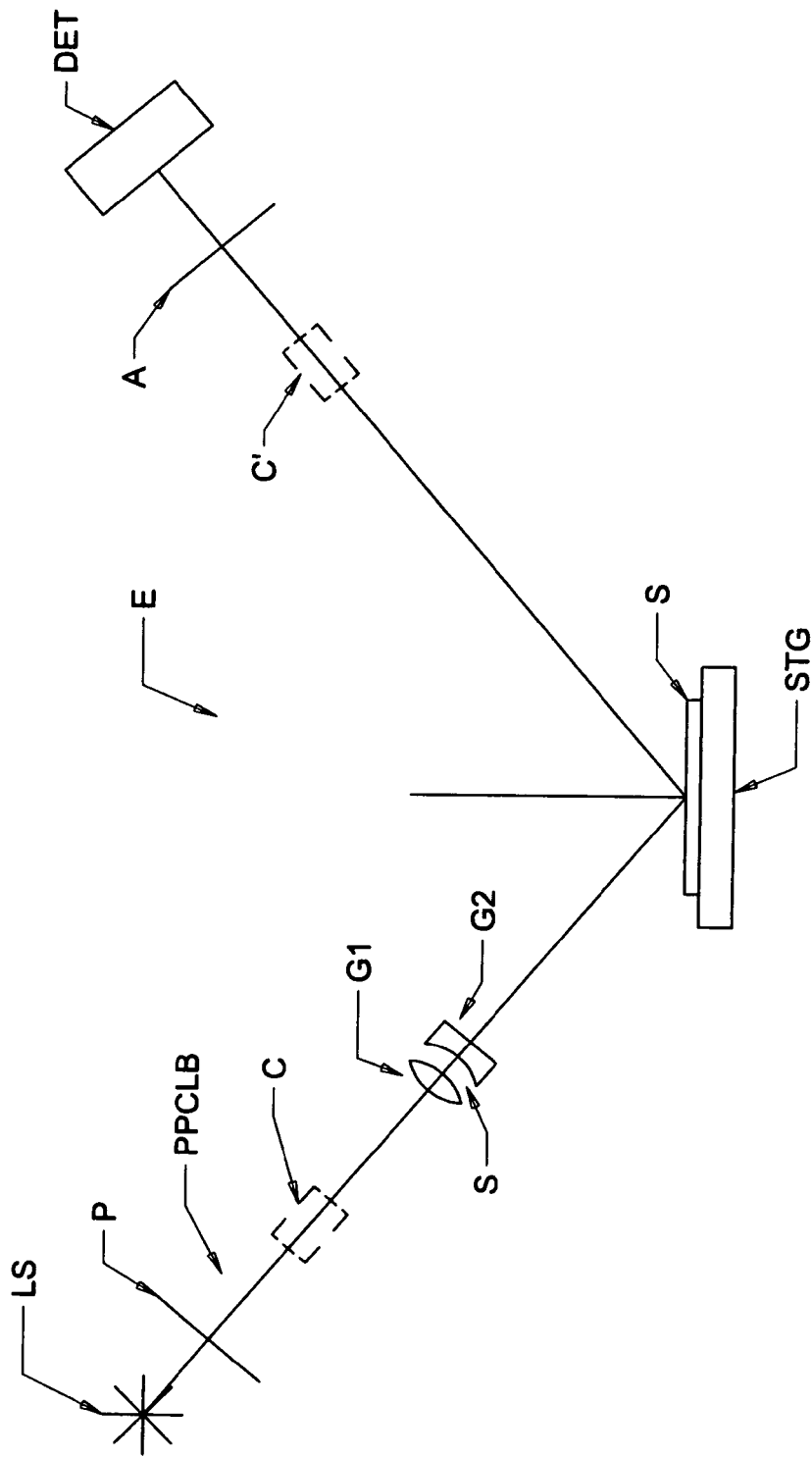
FIG. 4 is included to represent an ellipsometer, and the relationship of the lens groups thereto.

FIG. 4 is included to represent an ellipsometer (or polarimeter) (E), and the relationship of the lens groups (G1) (G2) thereto. Note the presence of a source (LS) of electromagnetic radiation, a polarizer (P), the leans groups (G1) (G2), a stage (STG) for supporting a sample (S), an analyzer (A) and a detector (DET). In use the source (LS) provides a beam of electromagnetic radiation which exiting the polarizer (P) is shown as (PPCLB). Optional compensators (C) (C') can also be present. The important thing to note is that the lens groups (G1) (G2) can be generally fixed in place with respect to the source (LS) and sample (S). It can happen in ellipsometers that physical design makes it difficult to mover the lens elements (G1) (G2). Thus, if the distance between the source (LS) and lens groups (G1) (G2) is improper to provide a focused beam on said sample (S), a problem can result. The present invention allows adjusting the spacing (S) between the lens groups (G1) and (G2) to overcome the problem.

In use, any of the polarizer (P), compensator (C) (C'), or analyzer (A) elements can be rotated or held stationary. For instance, when the polarizer (P) and analyzer (A) are held stationary and at least on compensator is rotated during data acquisition, the resulting system is termed a rotating compensator system. Likewise, if the polarizer (P) or analyzer (A) is rotated, the resulting system is termed a rotating polarizer or rotating analyzer system.

It is noted that removal of the polarizer (P), analyzer (A) and compensators (C) (C') from FIG. 4, provides a general configuration of a reflectometer or spectrophotometer. FIG. 4 is to be interpreted to show such.

The present invention lens system is applicable for use in any ellipsometer, polarimeter, reflectometer or spectrophotometer.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A method of minimizing the effect of aberration caused by a focusing lens system at a sequential plurality of image planes, thereby minimizing a beam spot size at a point whereat it impinges on an image plane, comprising the steps of:
   a) providing a source of electromagnetic radiation having a finite size, and a lens system located at an object distance from said source of electromagnetic radiation, such that an image of said source is formed at an image plane at an image distance from said lens system, said lens system comprising at least two groupings of lens elements, each grouping comprising a selection from the group consisting of:
      a single lens element; and
      a plurality of lens elements;
   said lens system further comprising means for releasably securing groupings of lens elements at intended distances from one another; and
   said lens system allowing for adjustment of distance between at least two, of said at least two, groupings of lens elements;
   b) configuring the system to position said source of electromagnetic radiation at an object distance from said lens system to direct a beam thereof through said lens system and impinge at said image plane;
   c) adjusting the spacing between at least two, of the at least two, groupings of lens elements so that the effects of aberration, hence, spot size of the beam where it impinges on said image plane become substantially minimized and releasably securing said at least two groupings of lens elements in position;
said method further comprising:
   d) configuring the system to position said source of electromagnetic radiation at an object distance from said lens system, which differes from that set in step b, to direct a beam thereof through said lens system and impinge at a resulting image plane;
   e) adjusting the spacing between at least two, of the at least two, groupings of lens elements so that the effects of aberration, hence, spot size of the beam where it impinges on a resulting image plane become substantially minimized, and releasably securing said at least two groupings of lens elements in position;
wherein said spacings in steps c and e between said at least two, of the at least two groupings of lens elements different.

2. An ellipsometer or polarimeter comprising:
   a source of electromagnetic radiation;
   a polarizer;
   a lens system;
   a sample support with a sample placed thereupon;
   an analyzer; and
   a detector;
said source of electromagnetic radiation having a finite size, and a lens system located at an object distance from said source of electromagnetic radiation, such that an image of said source is formed at an image plane at an image distance from said lens system, said lens system comprising at least two groupings of lens elements, each grouping comprising a selection from the group consisting of:
   a single lens element; and
   a plurality of lens elements;
said lens system further comprising means for releasably securing groupings of lens elements at intended distances from one another; and
said lens system allowing for adjustment of distance between two, of said at least two, groupings of lens elements to at least two different distances.

3. An ellipsometer or polarimeter system as in claim 2 in which the means for releasably securing groupings of lens elements at intended distances from one another comprises a tube in which said lens elements are placed, and in which at least the distance between two, of said at least two groupings of lens elements, is effected by the presence of one or more spacers therebetween.

4. An ellipsometer or polarimeter system as in claim 3, in which there are two groups of lens elements separated by a spacer.

5. An ellipsometer or polarimeter system as in claim 4, in which the number of lens elements in each group is independently selected from the group consisting of:
   a single lens element; and
   a plurality of lens elements.

6. An ellipsometer or polarimeter system as in claim 3, in which there are three groups of lens elements, each said group being separated by a spacer from an adjacent group.

7. An ellipsometer or polarimeter system as in claim 2, in which said one or more spacers are tubular in shape and sized to fit precisely inside said tubular shaped means for releasably securing groupings of lens elements at intended distances from one.

8. A reflectometer or spectrophotometer comprising:
   a source of electromagnetic radiation;
   a lens system;
   a sample support; and
   a detector;
said source of electromagnetic radiation having a finite size, and a lens system located at an object distance from said source of electromagnetic radiation, such that an image of said source is formed at an image plane at an image distance from said lens system, said lens system comprising at least two groupings of lens elements, each grouping comprising a selection from the group consisting of:
   a single lens element; and
   a plurality of lens elements;
said lens system further comprising means for releasably securing groupings of lens elements at intended distances from one another; and
said lens system allowing for adjustment of distance between two, of said at least two, groupings of lens elements to at least two different distances.

9. A reflectometer or spectrophotometer system as in claim 8 in which the means for releasably securing groupings of lens elements at intended distances from one another comprises a tube in which said lens elements are placed, and in which at least the distance between two, of said at least two groupings of lens elements, is effected by the presence of one or more spacers therebetween.

10. A reflectometer or spectrophotometer system as in claim 9, in which there are two groups of lens elements separated by a spacer.

11. A reflectometer or spectrophotometer system as in claim 10, in which the number of lens elements in each group is independently selected from the group consisting of:
   a single lens element; and
   a plurality of lens elements.

12. A reflectometer or spectrophotometer system as in claim 9, in which there are three groups of lens elements, each said group being separated by a spacer from an adjacent group.

13. An reflectometer or spectrophotometer system as in claim 8, in which said one or more spacers are tubular in shape and sized to fit precisely inside said tubular shaped means for releasably securing groupings of lens elements at intended distances from one.

14. A spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:

before said stage for supporting a material system;

after said stage for supporting a material system, and both before and after said stage for supporting a material system;

such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system;

said spectroscopic rotating compensator material system investigation system further comprising a lens system comprising at least two groupings of lens elements, each grouping comprising a selection from the group consisting of:

a single lens element; and a plurality of lens elements;

said lens system further comprising means for releasably securing groupings of lens elements at intended distances from one another; and said lens system allowing for adjustment of distance between two, of said at least two, groupings of lens elements to at least two different distances.

15. A spectroscopic rotating compensator material system investigation system as in claim 14 in which the means for releasably securing groupings of lens elements at intended distances from one another comprises a tube in which said lens elements are placed, and in which at least the distance between two, of said at least two groupings of lens elements, is effected by the presence of one or more spacers therebetween.

16. A spectroscopic rotating compensator material system investigation system as in claim 15, in which there are two groups of lens elements separated by a spacer.

17. A spectroscopic rotating compensator material system investigation system as in claim 16, in which the number of lens elements in each group is independently selected from the group consisting of:

a single lens element; and a plurality of lens elements.

18. A spectroscopic rotating compensator material system investigation system in claim 16, in which the number of lens elements in each group is independently selected from the group consisting of:

a single lens element; and a plurality of lens elements.

19. A spectroscopic rotating compensator material system investigation system as in claim 16, in which said one or more spacers are tubular in shape and sized to fit precisely inside said tubular shaped means for releasably securing groupings of lens elements at intended distances from one.

20. A spectroscopic rotating compensator material system investigation system as in claim 15, in which there are three groups of lens elements, each said group being separated by a spacer from an adjacent group.

* * * * *